(12) United States Patent  
Chang (10) Patent No.: US 7,115,737 B2
(45) Date of Patent: Oct. 3, 2006

(54) SOLID PHASE SYNTHESIS OF NOVEL BIARYL TRIAZINE LIBRARY BY SUZUKI CROSS COUPLING

(75) Inventor: Young-Tae Chang, New York, NY (US)

(73) Assignee: New York University, New York, NY (US)

(*) Notice: Subject to any disclaimer, the term of this patent is extended or adjusted under 35 U.S.C. 154(b) by 106 days.

(21) Appl. No.: 10/837,654

(22) Filed: May 4, 2004

(65) Prior Publication Data

US 2004/0225125 A1   Nov. 11, 2004

Related U.S. Application Data

(60) Provisional application No. 60/467,596, filed on May 5, 2003.

(51) Int. Cl.
   *C07D 251/18*   (2006.01)
   *C07D 251/30*   (2006.01)
   *C07D 251/38*   (2006.01)
   *C07D 251/40*   (2006.01)

(52) U.S. Cl. .................. 544/205; 544/206; 544/213

(58) Field of Classification Search ............... 544/205, 544/206, 213
   See application file for complete search history.

(56) References Cited

FOREIGN PATENT DOCUMENTS

WO   WO 03/032903 A2   4/2003
WO   WO 03/050237 A2   6/2003

OTHER PUBLICATIONS

Bork, J., et al., "Novel Orthogonal Strategy Toward Solid-Phase Synthesis of 1, 3,5-Substituted", Organic Letters, 2003, pp. 117-120, vol. 5, No. 2.

Bork, J., et al., "Palladium-Catalyzed Cross-Coupling Reaction of Resin-Bound Chlorotriazines", Tetrahedron Letters, 2003, pp. 6141-6144, vol. 44, 32.

Cocuzza, A. J., et al., "Use of the Suzuki Reaction for the Synthesis of Aryl-Substituted Heterocycles as Corticotropin-Releasing Hormone (CRH) Antagonists", Bioorganic & Medicinal Letters, 1999, pp. 1063-1066, vol. 9, No. 7.

Cooke, G., et al., Synthesis of 6-Aryl-2,4-Diamino-Pyrimidines and Triazines using Palladium Catalyzed Suzuki Cross-Coupling Reactions, TETRAHEDRON, 2001, pp. 2787-2789, vol. 57, No. 14.

Ding, S., et al., "A Combinatorial Scaffold Approach toward Kinase-Directed Heterocylce Libraries", Journal of the American Society, 2002, pp. 1594-1596, vol. 124, No. 8.

Moon, H., et al., "A Novel Microtubule Destabilizing Entity from Orthogonal Synthesis of Triazine Library and Zebrafish Embryo Screening", Journal of the American Chemical Society, 2002, pp. 11608-11609, vol. 124, No. 39.

Saito, S., et al., "Synthesis of Biaryls via a Nickel (0)-Catalyzed Cross-Coupling Reaction of Chloroarenes with Arylboronic Acids", Journal of Organic Chemistry, 1997, pp. 8024-8030, vol. 62, No. 23.

Schareina, T., et al., Combinatorial Libraries with P-functionalized aminopyridines: Ligands for the Preparation of Efficient C(aryl)-Cl Activation Catalysts, Angewandte Chemi, Interantional Edition, 2002, pp. 1521-1523, vol. 41, No. 9.

*Primary Examiner*—Venkataraman Balasubramanian
(74) *Attorney, Agent, or Firm*—Browdy and Neimark, PLLC (57) ABSTRACT

Two methods are used to produce diaryl trisubstituted triazines. In the first method, cyanuric chloride is first reacted with a 4-alkoxybenzylamine. The product of this reaction is then reacted with a resin-bound amine, such as 4-alkoxybenzylamine, to ensure that the final compound will be bound to a resin. The product of this reaction is then reacted with boronic acid to produce a trisubstituted diaryl triazine. In the second method, cyanuric chloride is reacted with a benzenealkanethiol. The product of this reaction is then reacted with a resin-bound amine, such as 4-alkoxybenzylamine, to ensure that the final compound will be bound to a resin. The product of this reaction is then reacted with m-CPBA to form a sulfone, which is then reacted with a 4-alkoxybenzylamine to form the desired trisubstituted biaryltriazine.

13 Claims, 4 Drawing Sheets

Figure 3. LC-MS Data of entry 8, compound 3a in Table 1.

Figure 4. LC-MS Data of entry 7, compound 3b in Table 1.

Figure 5. LC-MS data of entry 8, compound 3c in Table 1

SOLID PHASE SYNTHESIS OF NOVEL BIARYL TRIAZINE LIBRARY BY SUZUKI CROSS COUPLING

CROSS REFERENCED TO RELATED APPLICATIONS

This application claims priority from provisional application Ser. No. 60/467,596 filed May 5, 2003.

FIELD OF THE INVENTION

The present invention relates to a method for performing Suzuki cross-coupling of chlorotriazines on a solid support to produce an aryl-aryl triazine library.

BACKGROUND OF THE INVENTION

Aryl-aryl bond formation has elicited much interest in modern organic synthesis. This axially chiral bond is often found in natural products such as alkaloids (Bringmann et al., 1995; Furukawa et al., 1983; Bringmann et al., 2001), such as vancomycin, and is prevalent in biologically active parts of pharmaceuticals (Gallant et al., 2002; Sasaki et al., 2003, Hotzel et al., 2002) and agrochemical specialties (Ikegaya et al., 1999; Hatanaka et al., 1996), as well as in materials science (Bringmann et al., 1997; Lee et al., 2002; Messner et al., 2000). Development of a synthetic method for designing similarly structured compounds has been aided by advances in transition metal catalysis, namely, palladium-catalyzed cross-coupling reaction (Larock et al., 1995).

The present inventor has developed a unique orthogonal solid phase synthetic pathway for preparing a highly pure trisubstituted triazine library, in which three types of building blocks were assembled by chemically orthogonal reactions (Moon et al., 2002; Bork et al., 2003; Chang et al., U.S. Ser. No. 10/267,043, filed Oct. 9, 2002, the entire contents of which are hereby incorporated by reference). A series of compounds from the library, tubulyzines, demonstrated a significant biological activity by inhibiting tubulin polymerization (Moon et al., 2002). However, in this approach, bond formation was restricted to amine or several alcohol functionalities around the triazine scaffold.

The vinca alkaloids, including vinblastine and vincristine, have been used for treating cancers such as leukemias and lymphomas for a long time, and taxol derivatives have recently been used for treating breast cancers. However, these drugs are inherently toxic, especially neurotoxic, and the compounds are low in solubility and are not readily available in quantity. As most of the lead compounds originated from naturally occurring sources (plants, sponges, mollusks, bacteria), chemical modification might be a straightforward approach for improving the activity and properties of the drugs while reducing side effects. Serious efforts have been made to synthesize derivatives of vinca alkaloids, colchicines, taxol, and related compounds, but modification of the complicated natural products without adversely affecting utility has so far been difficult.

Solution-phase Suzuki couplings of heterocyclic aryl halides, such as halopyrimidines (Schomaker et al., 2001; Cooke et al., 2001), halopyridines (Zhang et al., 1998), halopurines (Ding et al., 2001; Havelkova et al., 2001), and halotriazines (Cooke et al., 2001; Janietz et al., 2002) have been studied in the literature. The Suzuki coupling has been further extended to solid phase (Hassan et al., 2002) both in halopyrimidines (Wade et al., 2003; Ding et al., 2002) and halopurines (Ding et al., 2002; Brun et al., 2002) yet has not been developed for the triazine scaffold.

SUMMARY OF THE INVENTION

It is an object of the present invention to overcome the aforesaid deficiencies in the prior art.

It is another object of the present invention to provide a triazine library including aryl-aryl substitution.

It is a further object of the present invention to perform Suzuki cross-coupling of triazines on a solid support.

Figure 1:
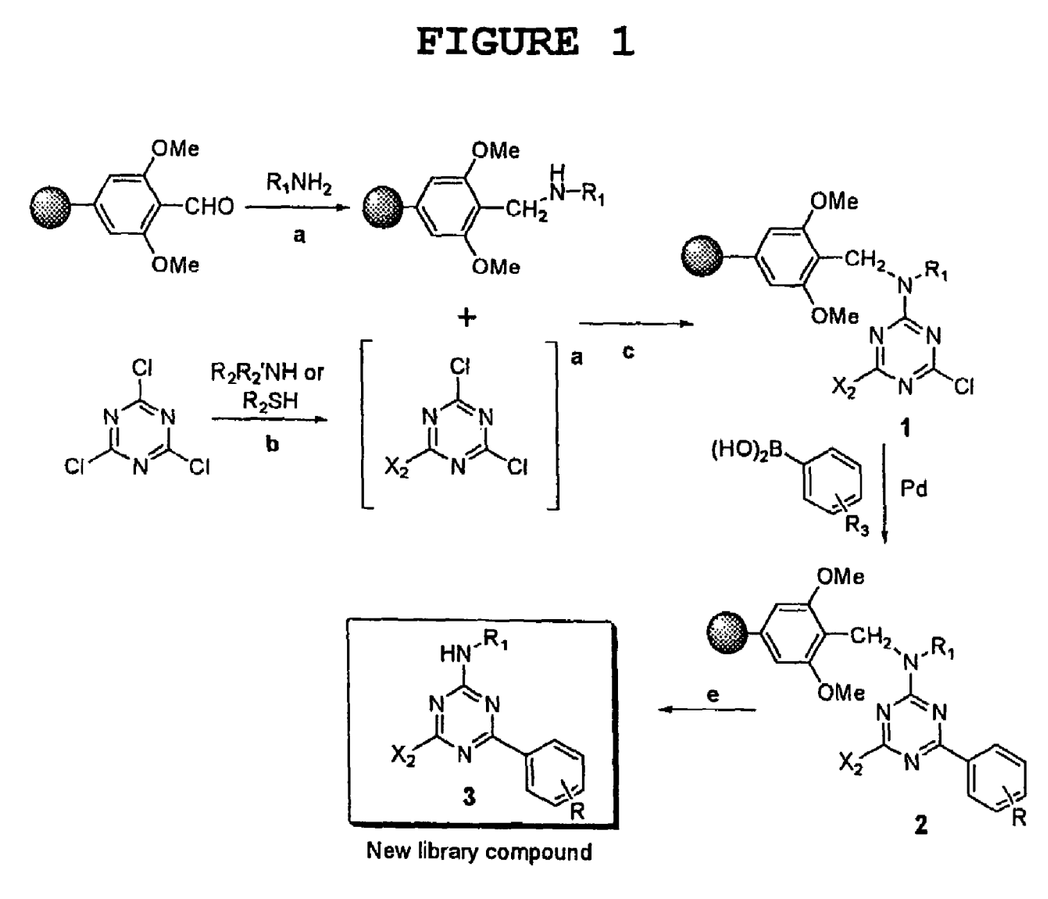
FIG. 1 shows orthogonal strategy for 1,3,5-trisubsituted triazines with Suzuki cross-coupling.

The present invention provides an efficient synthetic route for aryl-containing triazine compounds, as shown in FIG. 1. This was unexpected, because aryl chlorides typically show the least reactivity in the Suzuki reactions (I>OTf>Br>>Cl, Miyaura et al., 1995), it was discovered that chlorotriazine was sufficiently reactive, with percent conversion as high as 99%. This is particularly advantageous for library synthesis, since cyanuric chloride is lower priced and more commercially available than bromides or iodides.

With the advent of combinatorial chemistry, solid phase methodology is crucial in the synthesis of diversified triazine libraries, especially in the Suzuki reactions, since removal of unreacted boronic acid, palladium and ligand can be accomplished by sequential washing of the resin.

Two methods are used to produce the diaryl trisubstituted triazines of the present invention. In the first method, cyanuric chloride is first reacted with a 4-alkoxybenzylamine. The product of this reaction is then reacted with a resin-bound amine, such as 4-alkoxybenzylamine, to ensure that the final compound will be bound to a resin. The product of this reaction is then reacted with boronic acid to produce a trisubstituted diaryl triazine. In the second method, cyanuric chloride is reacted with a benzenealkanethiol. The product of this reaction is then reacted with a resin-bound amine, such as 4-alkoxybenzylamine, to ensure that the final compound will be bound to a resin. The product of this reaction is then reacted with meta-chloroperbenzoic acid to form a sulfone, which is then reacted with a 4-alkoxybenzylamine to form the desired trisubstituted biaryltriazine.

In the orthogonal approach described above, a primary amine was coupled to a 4-formyl-3-dimethoxyphenoxymethyl-functionalized polystyrene resin (PAL) by reductive amination. As shown in scheme 1 in FIG. 1, monosubstituted 4,6-dichlor-[1,3,5]-triazine, synthesized in solution, was loaded onto the solid support to give a chlorotriazine, 1, allowing for a final derivatization step. The Suzuki cross-coupling reaction accommodated this final position by generating a biaryl trisubstituted triazine 2.

DETAILED DESCRIPTION OF THE INVENTION

The present invention provides two synthetic strategies for making 1,3,5-trisubstituted aryltriazines that can be used for generating combinatorial triazine libraries. One approach is an orthogonal approach, shown in pathway 1 in Scheme 2, and the other is sulfone chemistry, illustrated in pathway 2 in Scheme 2. Using either one of these pathways, one can generate highly diversified and pure aryltriazines with versatility and ease.

The present invention uses Suzuki cross-coupling on a solid phase reaction to generate novel biaryl triazine libraries. Cross coupling between chlorotriazine and boronic acid on PAL resin was found to be a novel reaction which produced a useful triazine-based library. This reaction scheme can be used to extend diversity of already available triazine libraries, and to produce compounds which are mimics of naturally occurring biaryl alkaloid compounds.

Optimized conditions were found based on preliminary tests with resin bound 6-chloro-N,N'-bis-(4-methoxy-benzyl)-[1,3,5]-triazine-2,4-diamine and phenylboronic acid. It was crucial to choose an effective catalyst-ligand complex for the reaction to be performed defectively. Among several catalyst-complex systems, Pd (PPh$_3$) 4 (palladium tetrakistriphenylphosphine) proved to be the most functional and convenient catalyst, although other catalysts could also be used to catalyze this reaction. Pd(PPh$_3$)$_4$ demonstrated greater activity than the other catalysts tested, as shown in Table 1.

TABLE 1

Comparison of Suzuki Reaction Conditions

| | catalyst | ligand | base | Solvent | %[a] |
|---|---|---|---|---|---|
| 1 | Pd$_2$(dba)$_3$ | carbene[b] | Cs$_2$CO$_3$ | Dioxane | 5 |
| 2 | Pd$_2$(dba)$_3$ | phosphine[c] | Cs$_2$CO$_3$ | Dioxane | 92 |
| 3 | Pd(PPh$_3$)$_4$ | n/a | Cs$_2$CO$_3$ | Dioxane | 95 |
| 4 | Pd(PPh$_3$)$_4$ | n/a | Cs$_2$CO$_3$ | Toluene | 78 |
| 5 | Pd(PPh$_3$)$_4$ | n/a | t-BuOK | Dioxane | 30 |
| 6 | Pd(PPh$_3$)$_4$ | n/a | DIEA | Dioxane | 50 |
| 7 | Pd(PPh$_3$)$_4$ | n/a | K$_3$PO$_4$ | Toluene | 95 |
| 8 | Pd(PPh$_3$)$_4$ | n/a | K$_3$PO$_4$ | Toluene | nr[d] |

[a]purity 1–7 of entry 1 compound 3a of Table 2,
[b]1,3-Bis-(2,4,6-trimethyl-phenyl)-3H-imidazol-1-ium
[c]biphenyl-2-yl-dicyclohexyl-phosphane
[d]purity of entry 3 compound 3a of Table 2

It can be seen from Table 1 that other catalysts that can be used in the present invention include (Pd)$_2$(dba)$_3$, ligands such as carbene and phosphine, and bases such as CsCO$_2$O$_3$, t-BuOK, and K$_3$PO$_4$.

Under the conditions used as described hereinafter, Pd$_2$(dba)$_3$ with the carbene ligand had excessive activity, producing a high percentage of unknown impurities. While the phosphine ligand allowed for the reaction to proceed in comparable yields, to avoid excess material usage and extra preparation steps, commercially available Pd(PPh$_3$)$_4$ was chosen as the preferred catalyst for the method of the present invention. For general solubility of the reagents and performance, dioxane was found to be better than toluene as the solvent. To avoid shrinking the resin, aqueous base solutions were not tested under the conditions of the present method.

Use of dried potassium phosphate with Pd(PPh$_3$)$_4$ yielded high purity in preliminary experiments with phenylboronic acid. However, when tested with several other arylboronic acids, such as 3-formylphenylboronic acid, the reaction did not proceed very well and yielded starting material and many small impurities, suggesting that cesium carbonate was a better generalized base to use in this reaction. Thus, the optimized reaction condition is Pd(PPh$_3$)$_4$ with cesium carbonate in dioxane solvent.

Synthesis of disubstituted monochlorotriazine was followed by the known procedure (Moon et al., 2002; Bork et al., 2003). The Suzuki cross-coupling reaction accommodated this final position by generating a disubstituted aryltriazine 2. The catalyst was stored and dispensed within a glove box to prevent oxidation of Pd(0).

The reactions were heated to 90° C. for fifteen hours under argon gas atmosphere. Anhydrous dioxane was used to ensure efficiency of the reaction. Mild acidic cleavage of the resin bound molecule with 10% trfluoroacetic acid/dichloromethane (TFA/DCM) gave the final trisubstituted triazine product, 3. All of the products were analyzed for purity and identified by liquid chromatography mass spectroscopy (LC-MS) equipped with a diode array detector.

A variety of aryl boronic acids, represented in Table 2, were tested in the Suzuki reaction using optimal conditions. The sulfide substrate proved to be very valuable for library synthesis because it introduces a heterocyclic sulfone, another leaving group, which permits a final derivatization step. The present inventors previously demonstrated a generally higher purity for benzylsulfanyl triazines undergoing nucleophilic substitution than those of the 4-methyoxybenzylamine triazines, which suggested an increased reactivity at the chloro position of the benzylsulfanyl triazine. The comparison to the Suzuki cross-coupling reaction was extended by assessing a comparison of reactivity between the two substrates, amine and sulfide, as shown in Scheme 2, FIG. 2.

To further demonstrate the efficiency and usefulness of pathway 2, synthesis of the selected compounds in Table 2 was continued in the solid phase, using oxidation with m-CPBA of the benzylsulfide, followed by a replacement of benzylsulfone with 4-methoxybenzylamine. This served as a useful comparison for both pathways, since products 3a and 3c are identical compounds.

TABLE 2

Representative compounds

| | | purity (%) | | |
|---|---|---|---|---|
| entry | boronic acid | 3a | 3b | 3c |
| 1 | HO-B(OH)-phenyl | 95 | 98 | 96 |
| 2 | thiophene-B(OH)$_2$ | 93 | 95 | 95 |
| 3 | 3-formylphenyl-B(OH)$_2$ | 85 | 90 | 90[a] |
| 4 | 4-(hexafluoroisopropoxy)phenyl-B(OH)$_2$ | 90 | 99 | 96 |
| 5 | 4-methoxyphenyl-B(OH)$_2$ | 92 | 99 | 95 |

TABLE 2-continued

Representative compounds

| | | purity (%) | | |
|---|---|---|---|---|
| entry | boronic acid | 3a | 3b | 3c |
| 6 | HO-B(OH)-C6H4-C(CH3)3 | 95 | 98 | 95 |
| 7 | phenoxy-C6H4-B(OH)2 | 70 | 65 | 65 |
| 8 | HO-B(OH)-C6H4-F | 98 | 99 | 96 |

<sup>a</sup>oxidation of carbonyl yielded carboxylic acid as final 3c product

The representative arylboronic acids in Table 2 were found to be effective in preparing the desired compounds via the palladium catalyzed reactions in both pathways. The purity data correlate to the three final cleaved products of Scheme 1, namely, 3a, 3b, and 3c, with either 4-methoxybenzylamine or benzenemethanethiol as the $R_2$ substituent. 4-methoxybenzylamine was used as the $R_1$ resin-bound amine for all reactions.

Figure 2:
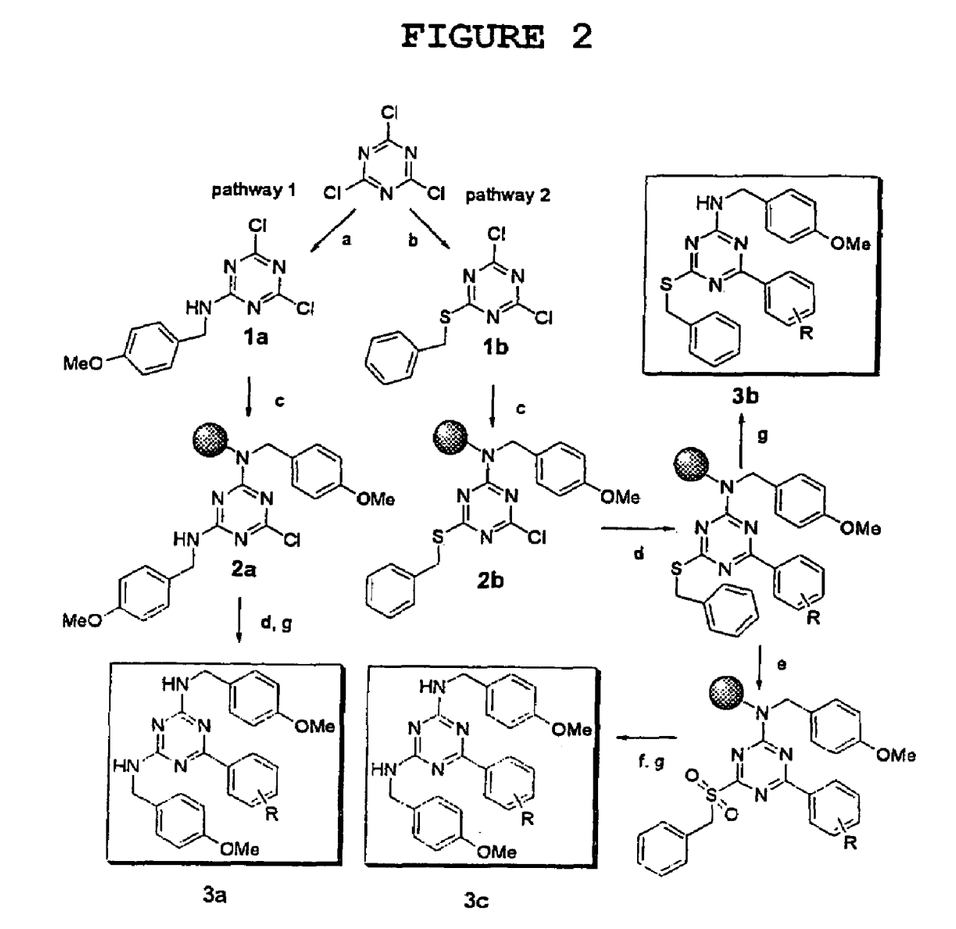
FIG. 2 shows two pathways for synthesis of diversified tri-substituted biaryl triazines.
Figure 3:
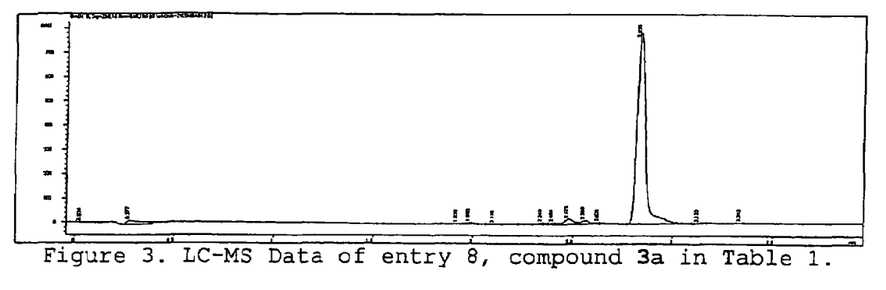
FIG. 3 shows LC-MS data from entry 8, compound 3a in Table 1.
Figure 4:
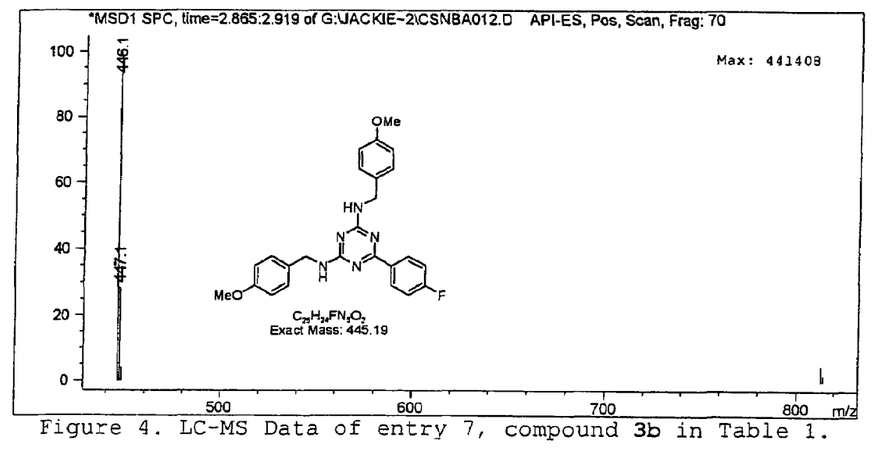
FIG. 4 shows LC-MS date of entry 7, compound 3b in Table 1.
Figure 5:
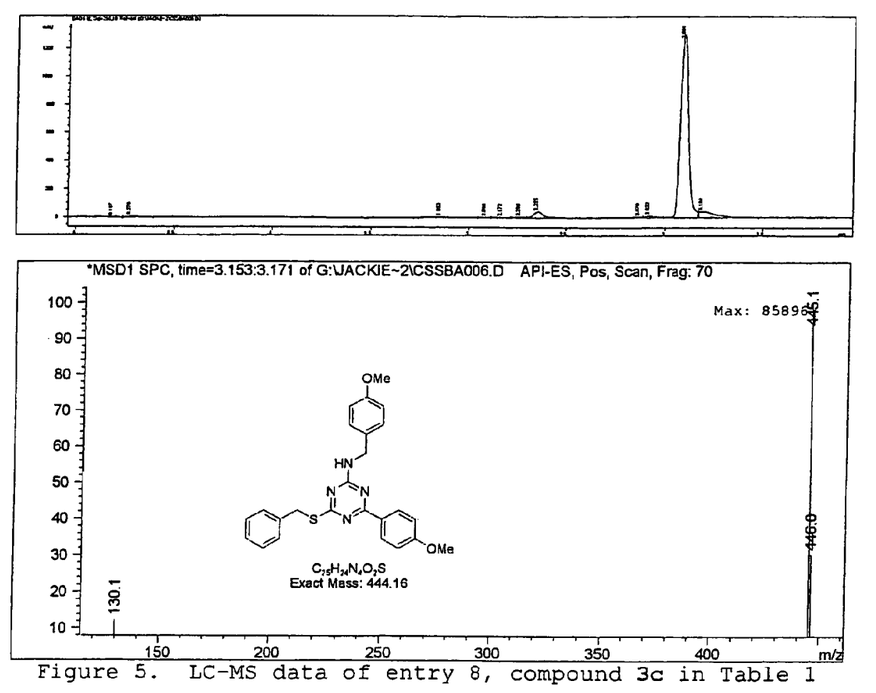
FIG. 5 shows LC-MS data of entry 8, compound 3c in Table 1.

In Scheme 2, the reagents and conditions were as follows:
(a) 4-methoxybenzylamine, tetrahydrofuran (THF), diisopropylethylamine (DiEA), 0° C.
(b) benzenemethanethiol, THF, DiEA, 0° C.
(c) resin-bound 4-methoxybenzylamine, THF, DiEA, 60° C., 2.5 hours
(d) boronic acid, Pd(PPh$_3$)$_4$, Cs$_2$CO$_3$, dioxane, 90° C., 15 hours
(e) m-CPBA, 1 N NaOH, dioxane, room temperature, eight hours
(f) 4-methoxybenzylaminde, DiEA, NMP:BuOH (1:1), 120° C. for three hours
(g) 10% TFA/DCM (dichloromethane), room temperature, 30 minutes.

In general, the 3b compounds exhibited higher purity than the 3a compounds, so that the final product 3c exhibited high purity. Entry 7 in Table 2 proved to have relatively low reactivity, primarily because of steric hindrance. In general, the results illustrate the broad tolerance of the reaction for arylboronic acids bearing a variety of substituents with both electron-withdrawing and electron-donating characteristics.

In Scheme 1, R is aryl or an alkyl substituent such as phenyl, phenoxy, methoxy, ethoxy, etc.; R1 is aryl, alkenyl, or alkyl; and X is aryl, alkyl, alkenyl amine, alcohol, or thiol.

The following are nonlimiting examples of amines that can be used in Scheme 1.

-continued

| | Structure |
|---|---|
| 15 |  |
| 16 |  |
| 17 |  |
| 18 |  |
| 19 |  |
| 20 |  |
| 21 |  |
| 22 |  |
| 23 |  |
| 24 |  |
| 25 |  |
| 26 |  |
| 27 |  |

-continued

| | Structure |
|---|---|
| 28 |  |
| 29 |  |
| 30 |  |
| 31 |  |
| 32 |  |
| 33 |  |
| 34 |  |
| 35 |  |
| 36 |  |
| 37 |  |
| 38 |  |
| 39 |  |
| 40 |  |
| 41 |  |

-continued

| | Structure |
|---|---|
| 42 | ⟩—NH₂ |
| 43 | HO⁀⟍⁀NH₂ |
| 44 | HO⟍⁀NH₂ |

The term "aryl" herein refers to aromatic cyclic compounds having up to 10 atoms, including carbon atoms, oxygen atoms, sulfur atoms, selenium atoms, etc. Aryl groups include, but are not limited to, groups such as phenyl, substituted phenyl, naphthyl, substituted naphthyl, in which the substituent is preferably lower alkyl, halogen, or lower alkyl. "Aryl" may also refer to fused rings systems having aromatic unsaturation. The fused ring systems can contain up to about 7 rings.

An "aryl group substituent" as used herein includes alkyl, cycloalkyl, cycloaryl, aryl, heteroaryl, optionally substituted with 1 or more, preferably 1 to 3, substituents selected from halo, haloalkyl, and alkyl, arylalkyl, heteroarylalkyl, alkenyl containing 1 to 2 double bonds, alkynyl containing 1 to 2 triple bonds, halo, hydroxy, polyhaloalkyl, preferably trifluoromethyl, formyl, alkylcarbonyl, arylcarbonyl, optionally substituted with 1 or more, preferably 1 to 3, substituents selected from halo, haloalkyl, alkyl, heteroarylcarbonyl, carboxyl, alkoxycarbonyl, aryloxycarbonyl, aminocarbonyl, alkylaminocarbonyl, dialkylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, amido, nitro, mercapto, alkylthio, arylthio, perfluoroalkylthio, thiocyano, isothiocyano, alkylsufinyl, alkylsulfonyl, arylsulfinyl, arylsulfonyl, aminosulfonyl, alkylaminosulfinyl, dialkylaminosulfonyl, and arylaminosulfonyl.

As used herein, alkyl, alkenyl and alkynyl carbon chains, if not specified, contain from 1 to 20 carbon atoms, preferably from 1 to 16 carbon atoms, and are straight or branched. Alkenyl carbon chains of from 1 to 20 carbon atoms preferably contain 1 to 8 double bonds; the alkenyl carbon chains of 1 to 16 carbon atoms preferably contain from 1 to 5 double bonds.

Alkynyl carbon chains of from 1 to 20 carbon atoms preferably contain 1 to 8 triple bonds, and the alkynyl carbon chains of 1 to 16 carbon atoms preferably contain 1 to 5 triple bonds. The alkyl, alkenyl, and alkynyl groups may be optionally substituted, with one or more groups, preferably alkyl group substituents that may be the same or different. As used herein, lower alkyl, lower alkenyl, and lower alkynyl refer to carbon chains having fewer than or equal to about 6 carbon atoms.

As used herein an alkyl group substituent includes halos, haloalkyl, preferably halo lower alkyl, aryl, hydroxy, alkoxy, aryloxy, alkoxy, alkylthio, arylthio, aralkyloxy, aralkylthio, carboxy, alkoxycarbonyl, oxo, and cycloalkyl.

For the present invention, "cyclic" refers to cyclic groups preferably containing from 3 to 19 carbon atoms, preferably 3 to 10 members, more preferably 5 to 7 members. Cyclic groups include hetero atoms, and may include bridged rings, fused rings, either heterocyclic, cyclic, or aryl rings.

The term "arylalkyl" as used herein refers to an alkyl group which is substituted with one or more aryl groups. Examples of arylalkyl groups include benzyl, 9-fluorenylmethyl, naphthylmethyl, diphenylmethyl, and triphenylmethyl.

"Cycloalkyl" as used herein refers to a saturated mono- or multicyclic ring system, preferably of 3 to 10 carbon atoms, more preferably from 3 to 6 carbon atoms. Cycloalkenyl and cycloalkynyl refer to mono- or multicyclic ring systems that respectively include at least one double bond and at least one triple bond. Cycloalkenyl and cycloalkynyl groups may preferably contain 3 to 10 carbon atoms, with cycloalkenyl groups more preferably containing 4 to 7 carbon atoms and cycloalkynyl groups more preferably containing 8 to 10 carbon atoms. The ring systems of the cycloalkyl, cycloalkenyl and cycloalkynyl groups may be composed of one ring or two or more rings which may be joined together in a fused, bridged, or spiro-connected fashion, and may be optionally substituted with one or more alkyl group substituents.

The term "heteroaryl" for purposes of the present application refers to a monocyclic or multicyclic ring system, preferably about 5 to about 15 members, in which at least one atom, preferably 1 to 3 atoms, is a heteroatom, that is, an element other than carbon, including nitrogen, oxygen, or sulfur atoms. The heteroaryl may be optionally substituted with one or more, preferably 1 to 3, aryl group substituents. Exemplary heteroaryl groups include, for example, furanyl, thienyl, pyridyl, pyrrolyl, N-methylpyrrolyl, quinolyinyl and isoquinolinyl.

The term "heterocyclic" refers to a monocyclic or multicyclic ring system, preferably of 3 to 10 members, more preferably 4 to 7 members, where one or more, preferably 1 to 3, of the atoms in the ring system is a heteroatom, i.e., an atom that is other than carbon, such as nitrogen, oxygen, or sulfur. The heterocycle may be optionally substituted with one or more, preferably 1 to 3, aryl group substituents. Preferred substituents of the heterocyclic group include hydroxy, alkoxy, halo lower alkyl. The term heterocyclic may include heteroaryl. Exemplary heterocyclics include, for example, pyrrolidinyl, piperidinyl, alkylpiperidinyl, morpholinyl, oxadiazolyl, or triazolyl.

The nomenclature alkyl, alkoxy, carbonyl, etc, is used as is generally understood by those skilled in this art. As used herein, aryl refers to saturated carbon chains that contain one or more carbon atoms; the chains may be straight or branched or include cyclic portions or may be cyclic.

The term "halogen" or "halide" includes F, Cl, Br, and I. This can include pseudohalides, which are anions that behave substantially similarly to halides. These compounds can be used in the same manner and treated in the same manner as halides. Pseudohalides include, but are not limited to, cyanide, cyanate, thiocyanate, selenocyanate, trifluoromethyl, and azide.

The term "haloalkyl" refers to a lower alkyl radical in which one or more of the hydrogen atoms are replaced by halogen, including but not limited to, chloromethyl, trifluoromethyl, 1-chloro-2-fluoroethyl, and the like.

"Haloalkoxy" refers to RO⁻ in which R is a haloalkyl group.

The term "sulfinyl" refers to —S(O)—. "sulfonyl" refers to —S(O)₂—.

"Aminocarbonyl" refers to —C(O)NH₂.

"Alkylene" refers to a straight, branched, or cyclic, preferably straight or branched, bivalent aliphatic hydrocarbon group, preferably having from 1 to about 20 carbon atoms. The alkylene group is optionally substituted with one or more alkyl group substituents. There may be optionally inserted along the alkylene group one or more oxygen, sulfur, or substituted or unsubstituted nitrogen atoms, wherein the nitrogen substituent is alkyl. Exemplary alkylene groups include methylene, ethylene, propylene, cyclohexylene, methylenedioxy, and ethylenedioxy. The term "lower alkylene" refers to alkylene groups having from 1 to 6 carbon atoms. Preferred alkylene groups are lower alkylene, with alkylene of 1 to 3 atoms being particularly preferred.

The term "alkenylene" as used herein refers to a straight, branched or cyclic, preferably straight or branched, bivalent aliphatic hydrocarbon group, preferably having from about 1 to 20 carbon atoms and at least one double bond. The alkenylene group is optionally substituted with one or more alkyl group substituents. There may be optionally inserted along the alkenylene group one or more oxygen, sulfur, or substituted or unsubstituted nitrogen atoms, where the nitrogen substituent is alkyl as previously described.

As used herein, "alkynylene" refers to a straight, branched or cyclic bivalent aliphatic hydrocarbon group having from 1 to about 20 carbon atoms and at least one triple bond. The alkynylene group is optionally substituted with one or more alkyl group substituents. There may be optionally inserted along the alkynylene group one or more oxygen, sulfur, or substituted or unsubstituted nitrogen atoms, where the nitrogen substituent is alkyl. The term "lower alkynylene" refers to alkynylene groups having from 2 to 6 carbon atoms.

The term "arylene" as used herein refers to a monocyclic or polycyclic bivalent aromatic group preferably having from 1 to 20 carbon atoms and at least one aromatic ring. The arylene group is optionally substituted with one or more alkyl group substituents. There may be optionally inserted around the arylene group one or more oxygen, sulfur, or substituted or unsubstitued nitrogen atoms, where the nitrogen substituent is alkyl.

"Heteroarylene" refers to a bivalent monocyclic or multicyclic ring system, preferably of about 5 to about 15 members, wherein one or more of the atoms in the ring system is a heteroatom. The heteroarylene may be optionally substituted with one or more aryl group substituents.

As used herein, "alkylidene" refers to a bivalent group, such as =CR'R", which is attached to one atom of another group, forming a double bond. "Arylalkylidene" refers to an alkylidene group in which either R' or R" is an aryl group.

As used herein, when any particular group, such as phenyl or pyridyl, is specified, this means that the group is substituted or unsubstituted. Preferred substituents, where not specified, are halo, halo lower alkyl, and lower alkyl.

The term "library" refers to a collection of diverse compounds, in the present case, based upon a triazine scaffold.

General

Unless otherwise noted, materials and solvents were obtained from commercial suppliers and were used without further purification. Anhydrous tetrahydrofuran (THF), 1-methyl-2-pyrrolidinone (NMP) from Acros and anhydrous 1,4-dioxane from Aldrich were used as reaction solvents without any prior purification. PAL-aldehyde resin from Midwest Bio-Tech was used as the solid support. For, the synthesis of building block I, general coupling reactions were performed through solution phase chemistry and were purified by flash column chromatography on Merck silica gel 60-PF$_{245}$. All products were identified by LC-MS from Agilent Technology using a C18 column (20×4.0 mm), with a gradient of 5–95% CH$_3$CN (containing 1% acetic acid)-H$_2$O (containing 1% acetic acid) as eluant.

Equipment

Thermal reactions were performed using a standard heat block from VWR scientific Products using 4 mL vials. Resin filteration procedures were carried out using 70μ PE frit cartridge from Applied Seprations.

General Procedure

Loading of Amine onto PAL Resin via Reductive Amination.

To a suspension of 4-formyl-3,5-dimethoxyphenoxymethyl-functionalized polystyrene resin (PAL) (1.0 g, 1.1 mmol) in THF (40 mL) was added a primary amine (5.5 mmol), followed by the addition of AcOH (0.9 mL). After shaking at room temperature for 1 hour, NaHB(OAc)$_3$ (1.63 g, 7.7 mmol) was added, and the reaction continued shaking at room temperature for 8 hours. Using a PE frit cartridge, the solvents and excess reagents were filtered out and washed with DMF, MC and MeOH (20 mL×3), ending with a final washing with MC and dried under nitrogen gas.

Synthesis of (4,6-Dichloro-[1,3,5]triazin-2-yl)-(4-methoxybenzyl)-amine.

To a solution of cyanuric chloride (1.5 g, 8.13 mmol) in THF (50 mL) Diisopropyethylamine (1.56 mL, 8.94 mmol) was added. The solution was placed in an ice-water bath (0° C.). Using a syringe, 4-methoxy-benzyl amine (1.16 mL, 8.94 mmol) dissolved in THF (150 mL) was slowly dripped into the reaction mixture. The reaction stirred at 0° C. for 3 hours. The crude compound was purified by column chromatography initially eluting with EA:Hexane (1:6). Compound was obtained as a white solid.

Synthesis of 2-Benzylsulfanyl-4,6-dichloro-[1,3,5]triazine.

To a solution of cyanuric chloride (2 g, 10.8 mmol) in THF (50 mL), diisopropylethylamine (1.1 eq.) was added. While cooling in an ice-water bath (0° C.), the α-toluenethiol (1.25 g, 10.1 mmol), dissolved in THF (150 mL), was slowly dripped into the reaction vessel via an additional funnel. The reaction was stirred at 0° C. for 3 hours. The reaction mixture was evaporated in reduced pressure. The crude compound was purified by column chromatography initially eluting with DCM:Hexane (1:4). Compound was obtained as oil.

Resin Capture of Triazine Scaffold via Amine Substitution. (a) To a suspension of the PAL-resin-bound amine (125 mg, 0.132 mmol) in THF (2.5 mL) was added the 4,6-Dichloro-[1,3,5]triazin-2-yl-4-methoxy-benzyl-amine (125 mg, 0.91 mmol), followed by addition of diisopropylethylamine (0.15 mL). The reaction was placed in a heating block set at 60° C. for 2.5 hours. The solvents and excess reagent were filtered through a PE frit cartridge and washed with DMF, DCM, MeOH (3 mL×3), consecutively, ending with a final washing with DCM (3 mL), and dried under nitrogen gas. (b) To a suspension of the PAL-resin-bound amine (125 mg, 0.132 mmol) in THF (2.5 mL) was added the 2-Benzylsulfanyl-4,6-dichloro-[1,3,5]triazine (125 mg), followed by addition of diisopropylethylamine (0.15 mL). The reaction was placed in a heating block set at 60° C. for 2.5 hours. The solvents and excess reagent were filtered through a PE frit cartridge and washed with DMF, DCM, MeOH (3 mL×3), consecutively, ending with a final washing with DCM (3 mL), and dried under nitrogen gas.

Nucleophilic Aromatic Substitution.

To a suspension of the resin-bound scaffold (10 mg, 11 μmol) in NMP (0.25 mL) was added an amine (0.2 mmol), followed by the addition of n-butanol (0.25 mL) and diisopropylamine (30 µL, 0.22 mmol). The reaction was placed in a heating block set at 120° C. for 3 hrs. The excess reagents were filtered through a PE frit cartridge and washed with DMF, DCM, MeOH (1 mL×3), consecutively, ending with a final washing with DCM (1 mL).

Suzuki Coupling.

$Pd(PPh_3)_4$ (7 mg, 6.06 µmol) was dispensed to pre-weighed resin-bound triazine scaffold (10 mg, 11 µmol) and $Cs_2CO_3$ (35 mg, 0.1 mmol) in a glove box. Dioxane (1 mL) was distributed to each reaction vial. The reaction was placed in a heating block, within a vinyl bag previously purged with argon gas, at 90° C. for 15 hrs The excess reagents were filtered through a PE frit cartridge and washed with sodium diethyldithiocarbamate in DMF solution (1 mL×5), DMF (1 mL×1), DCM, MeOH (1 mL×3), consecutively, ending with a final washing with DCM (1 mL).

Activation of Final Substitution Site by Oxidation of Thioether to Sulfone.

To a solution of m-CPBA (70%, 270 mg, 1.1 mmol) in 1,4-dioxane (8.82 mL), cooled to 0° C. and stirring, was added a NaOH (1.09 mL, 1N) aqueous solution. The solution of m-CPBA in dioxane solution was added to the resin (125 mg, 0.13 mmol) and gently shaken for 8 hrs at room temperature. The solution was filtered out with a PE frit cartridge and washed with 1,4-dioxane (3 mL×3) DCM, MeOH (3 mL×3), alternatively, ending with a final washing with DCM (3 mL) and dried under nitrogen gas. A final substitution followed at this site.

Resin Cleavage

10% TFA in DCM was added to the resin, shaking at room temperature for 30 min. The compound was filtered from the resin, washed with DCM (200 µL) and evaporated under a vacuum.

The diarylsubstituted triazine libraries of the present invention can be developed as drug candidates and can be used for developing new catalysts or chemo sensors.

The foregoing description of the specific embodiments will so fully reveal the general nature of the invention that other can, by applying current knowledge, readily modify and/or adapt for various application such specific embodiments without undue experimentation and without departing from the generic concept. Therefore, such adaptations and modifications should and are intended to be comprehended within the meaning and range of equivalents of the disclosed embodiments.

It is to be understood that the phraseology or terminology employed herein is for the purpose of description and not of limitation. The means and materials for carrying out various disclosed functions may take a variety of alternative forms without departing from the invention.

Thus, the expressions "means to . . . " and "means for . . . " as may be found in the specification above and/or in the claims below, followed by a functional statement, are intended to define and cover whatever structural, physical, chemical, or electrical element or structures which may now or in the future exist for carrying out the recited function, whether or nor precisely equivalent to the embodiment or embodiments disclosed in the specification above. It is intended that such expressions be given their broadest interpretation.

REFERENCES (1) (a) Bringmann, G.; Pokorny, F. *In the Alkaloids*; Cordell, G. A., Ed.; Academic Press: New York, 1995; Vol. 46, p 127. (b) Furukawa, H,; Wu, T. S.; Ohta, T. *Chem. Pharm. Bull.* 1983, 31, 4202–4205. (c) Bringmann, G.; Günther, C.; Ochse, M.; Schupp, O.; Tasler, S. *Prog. Chem. Org. Nat. Prod.* 2001, 82, 1–293.

(2) (a) Gallant, M.; Carriére, M. C.; Chateauneuf, A.; Denis, D.; Gareau, Y.; Godbout, C.; Greig, G.; Juteau, H.; Lachance, N.; Lacombe, P.; Lamontagne, S.; Metters, K. M.; Rochette, C.; Ruel, R.; Slipetz, D.; Sawyer, N.; Tremblay, N.; Labelle, M. *Biorg. Med. Chem. Lett.* 2002, 12, 2583–2586. (b) Sasaki, S.; Cho, N.; Nara, Y.; Harada, M.; Endo, S.; Suzuki, N.; Furuya, S.; Fujino, M. *J. Med. Chem.* 2003, 46, 113–124. (c) Hotzel, A.; Schmid, D. G.; Nicholson, G. J.; Graeme, J.; Stevanovic, S.; Schimana, J.; Gebhardt, K.; Fiedler, H. S.; Jung, G. *J. Antibio.* 2002, 55, 571–577.

(3) (a) Ikegaya, K.; Ozaki, M.; Kawashima, T.; Miura, I.; Muramatsu, N. Preparation of biarylalkylenecarbamic acid derivatives as agricultural and horticultural fungicides. PCT Int. Appl, WO9910317; 1999. (b) Hatanaka, Y.; Hagiwara, E.; Gouda, K.; Hiyama, T. Process of producing unsaturated organic compounds such as biaryls or arylpyridine derivative by coupling of organohalosilane with halobenzenes or halopyridines. PCT Int. Appl. WO9628401; 1996.

(4) (a) Bringmann, G.; Stowasser, R.; Goebel, L. *J. Organomet. Chem.* 1997, 544, 7–13. (b) Lee, D. H.; Im, J. H.; Lee, J. H.; Hong, J. I. *Tetrahedron Lett.* 2002, 43, 9637–9640. (c) Messner, M.; Kozhushkov, S.; De Meijere, A. *Eur. J. Org. Chem.* 2000, 1137–1155.

(5) (a) Larock, R. C. *Comprehensive Organic Transformations,* 2nd ed., Wiley-VCH: New York; 1999, pp 362–364. (b) Miyaura, N.; Suzuki, A. *Chem. Rev.* 1995, 95, 2457.

(6) Moon, H.; Jacobson, E.; Khersonsky, S. M.; Luzung, M.; Walsh, D.; Xiong, W.; Lee, J. W.; Parikh, P.; Lam, J. C.; Kang, T. W.; Rosania, G. F.; Schier, A.; Chang, Y. T. *J. Am. Chem. Soc.* 2002, 124, 11608–11609.

(7) Bork, J. T.; Lee, J. W.; Khersonsky, S. M.; Moon, H. S.; Chang, Y. T. *Org. Lett.* 2003, 5, 117–120.

(8) Schomaker, J. M.; Delia, T. J. *J. Org. Chem.* 2001, 66, 7125–7128.

(9) Cooke, G.; de Cremiers, A.; Rotello, V. M.; Tarbit, B.; Vanderstraeten, P. E. *Tetrahedron* 2001, 57, 2787–2789.

(10) (a) Zhang, H.; Chan, K. S. *Tetrahedron Lett.* 1996, 37, 1043–1044. (b) Zhang, H.; Kwong, F. Y.; Tian, Y.; Chan, K. S. *J. Org. Chem.* 1998, 63, 6886–6890.

(11) (a) Ding, S.; Gray, N. S.; Ding, Q.; Schultz, P. G. *Tetrahedron Lett.* 2001, 42, 8751–8755. (b) Havelková, M.; Dvořák, D.; Hocek, M. *Synthesis* 2001, 11, 1704–1710.

(12) Janietz, D.; Bauer, M. *Synthesis* 1993, 1, 33–34.

(13) Hassan, J.; Sévignon, M.; Gozzi, C.; Schulz, E.; Lemaire, M. *Chem. Rev.* 2002, 102, 1539–1469.

(14) Wade, J; Krueger, C. A. *J. Comb. Chem.,* 2003, ASAP article.

(15) Ding, S.; Gray, N. S.; Wu, X.; Ding, Q.; Schultz, P. G. *J. Amer. Chem. Soc.* 2002, 124, 1594–1596.

(16) Brun, V.; Legraverend, M.; Grierson, D. S. *Tetrahedron* 2002, 58, 7911–7923.

(17) Miyaura, N.; Suzuki, A. *Chem. Rev.* 1995, 95, 2457–2483.

What is claimed is:

1. A method for producing trisubstituted biaryl triazines comprising:
   a. reacting cyanuric chloride with a 4-alkoxybenzyl ámine;
   b. reacting the product of step (a) with a resin-bound amine;

c. reacting the product of step (b) with an arylboronic acid, catalyst, ligand, and base to produce a trisubstituted biaryltriazine.

2. The method according to claim 1 wherein the 4-alkoxybenzylamine is 4-methoxybenzylamine.

3. The method according to claim 1 wherein the arylboronic acid is selected from the group consisting of and

4. The method according to claim 1 wherein the amine is selected from the group consisting of

| | Structure |
|---|---|
| 1 | |
| 2 | |
| 3 | |

-continued

| | Structure |
|---|---|
| 4 | |
| 5 | |
| 6 | |
| 7 | |
| 8 | |
| 9 | |
| 10 | |
| 11 | |
| 12 | |
| 13 | |
| 14 | |
| 15 | |
| 16 | |

|    | Structure |
|----|-----------|
| 17 | 4-fluorobenzylamine |
| 18 | 2-fluorobenzylamine |
| 19 | isopentylamine (3-methylbutan-1-amine) |
| 20 | isopropylamine |
| 21 | 4-methoxybenzylamine |
| 22 | 3-methoxybenzylamine |
| 23 | 4-methoxyphenethylamine |
| 24 | 4-methylbenzylamine |
| 25 | (4-methylcyclohexyl)methanamine |
| 26 | 1-(4-nitrophenyl)piperazine |
| 27 | octylamine |
| 28 | phenethylamine |
| 29 | piperidine |

|    | Structure |
|----|-----------|
| 30 | (benzo[d][1,3]dioxol-4-yl)methanamine |
| 31 | pyrrolidine |
| 32 | morpholine |
| 33 | allylamine |
| 34 | benzylamine |
| 35 | butylamine |
| 36 | cyclohexylmethanamine |
| 37 | cyclohexylamine |
| 38 | 4-methoxybenzylamine |
| 39 | phenethylamine |
| 40 | 4-fluorobenzylamine |
| 41 | 4-aminocyclohexanol |
| 42 | isopropylamine |
| 43 | 3-aminopropan-1-ol and |
| 44 | 2-aminoethanol. |

5. A method for preparing a trisubstituted biaryl triazine compound comprising:
(a) reacting cyanuric chloride with a benzenealkanethiol;
(b) reacting the product of step (a) with a resin-bound amine;
(c) reacting the product of step (b) with a arylboronic acid to obtain a trisubstituted biaryl triazine compound;
(d) reacting the product of step (c) with m-CPBA to obtain a sulfone biaryltriazine; and
(e) reacting the product of step (d) with an amine to produce a trisubstituted biaryltriazine.

6. The method according to claim 4 wherein the amine is selected from the group consisting of

| | Structure |
|---|---|
| 1 |  |
| 2 |  |
| 3 |  |
| 4 |  |
| 5 |  |
| 6 |  |
| 7 |  |
| 8 |  |
| 9 |  |
| 10 |  |
| 11 |  |
| 12 |  |

-continued

| | Structure |
|---|---|
| 13 |  |
| 14 |  |
| 15 |  |
| 16 |  |
| 17 |  |
| 18 |  |
| 19 |  |
| 20 |  |
| 21 |  |
| 22 |  |
| 23 |  |
| 24 |  |

-continued

| | Structure |
|---|---|
| 25 |  |
| 26 |  |
| 27 |  |
| 28 |  |
| 29 |  |
| 30 |  |
| 31 |  |
| 32 |  |
| 33 |  |
| 34 |  |
| 35 |  |
| 36 |  |
| 37 |  |
| 38 |  |

-continued

| | Structure |
|---|---|
| 39 |  |
| 40 |  |
| 41 |  |
| 42 |  |
| 43 |  and |
| 44 | . |

7. A method for preparing a trisubstituted biaryl triazine compound comprising reacting a disubstituted monochlorotriazine of formula 1 with an aryl boronic acid to produce a diarylsubstituted triazine of formula 3 wherein R and $R_1$ are selected from the group consisting of phenyl substituted with at least one of F, Cl, methoxy, ethoxy, trifluoromethyl and $C_1$–$C_6$ alkyl, and benzyl substituted with at least one of F, Cl, methoxy, ethoxy, trifluoromethyl, and $C_1$–$C_6$ alkyl; and $X_2$ is selected from the group consisting of amines; alcohols; thiols; $C_1$–$C_{20}$ alkyl; phenyl substituted with at least one of F, Cl, methoxy, ethoxy, trifluoromethyl and $C_1$–$C_6$ alkyl; and benzyl substituted with at least one of F, Cl, methoxy, ethoxy, trifluoromethyl, and $C_1$–$C_6$ alkyl.

8. The method according to claim 1 wherein the catalyst is a palladium catalyst.

9. The method according to claim 8 wherein the catalyst is palladium tetrakistriphenylphosphine.

10. The method according to claim 8 wherein the catalyst is selected from the group consisting of $Pd_2(dba)_3$, $Pd(PPh_3)_4$ with a carbene or phosphine ligand, and with a base.

11. The method according to claim 9 wherein the base is $Ca_2CO_3$, tBuOK, or $K_3PO_4$.

12. The method according to claim 9 wherein the catalyst further comprises cesium carbonate in dioxane solvent.

13. The method according to claim 8 wherein the aryl boronic acid is selected from the group consisting of and

* * * * *